(12) United States Patent
Kaufman et al.

(10) Patent No.: US 11,992,495 B2
(45) Date of Patent: May 28, 2024

(54) ENHANCING GABA'S ABILITY TO MODULATE IMMUNE RESPONSES

(71) Applicant: THE REGENTS OF THE UNIVERSITY OF CALIFORNIA, Oakland, CA (US)

(72) Inventors: Daniel Kaufman, Los Angeles, CA (US); Jide Tian, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 16/625,181

(22) PCT Filed: Jun. 20, 2018

(86) PCT No.: PCT/US2018/038428
§ 371 (c)(1),
(2) Date: Dec. 20, 2019

(87) PCT Pub. No.: WO2018/236955
PCT Pub. Date: Dec. 27, 2018

(65) Prior Publication Data
US 2020/0138830 A1 May 7, 2020

Related U.S. Application Data

(60) Provisional application No. 62/524,338, filed on Jun. 23, 2017.

(51) Int. Cl.
| | |
|---|---|
| A61K 31/5517 | (2006.01) |
| A61K 9/20 | (2006.01) |
| A61K 31/5513 | (2006.01) |
| A61K 31/57 | (2006.01) |
| A61P 29/00 | (2006.01) |
| A61P 37/02 | (2006.01) |

(52) U.S. Cl.
CPC .......... *A61K 31/5517* (2013.01); *A61K 9/20* (2013.01); *A61K 31/5513* (2013.01); *A61K 31/57* (2013.01); *A61P 29/00* (2018.01); *A61P 37/02* (2018.01)

(58) Field of Classification Search
CPC .......... A61K 31/5513; A61K 31/5517; A61K 31/57; A61K 9/20; A61K 2300/00; A61K 45/06; A61P 37/02; A61P 29/00
See application file for complete search history.

(56) References Cited

U.S. PATENT DOCUMENTS

| 4,786,505 A | 11/1988 | Lovgren et al. | |
|---|---|---|---|
| 4,853,230 A | 8/1989 | Lovgren et al. | |
| 5,017,575 A * | 5/1991 | Golwyn | A61K 31/55 514/220 |
| 6,350,769 B1 | 2/2002 | Kaufman et al. | |
| 8,722,667 B2 | 5/2014 | Glick et al. | |

FOREIGN PATENT DOCUMENTS

| CN | 102458405 A | 5/2012 |
|---|---|---|
| WO | WO-0050034 A1 | 8/2000 |
| WO | WO-2007093183 A2 | 8/2007 |
| WO | WO-2012050907 A2 | 4/2012 |
| WO | WO-2017066240 A1 | 4/2017 |

OTHER PUBLICATIONS

Bhat et al., *Inhibitory role for GABA in autoimmune inflammation*, 107(6) PNAS 2580-2585 (Feb. 9, 2010).
Bowery et al., *$GABA_B$ Receptor Pharmacology*, 33 Annu. Rev. Pharmacol. Toxicol. 109-147 (1993).
Crowley et al., *Inhibiting neuroinflammation: The role and therapeutic potential of GABA in neuro-immune interactions*, 54 Brain, Behavior, and Immunity 260-277 (2016).
Dienz et al., *The effects of IL-6 on CD4 T cell responses*, 130(1) Clinical Immunology 27-33 (Jan. 1, 2009).
Erdö et al., *γ-Aminobutyric Acid Outside the Mammalian Brain*, 54(2) Journal of Neurochemistry 363-372 (Feb. 1998) (First Page Only).
Erlander et al., *Two genes encode distinct glutamate decarboxylases*, 7(1) Neuron. 91-100 (Jul. 1991) (Abstract Only).
Extended European Search Report in EP Application No. 18821455.5 (dated Mar. 9, 2021).
Forkuo et al., *Alleviation of Multiple Asthmatic Pathologic Features with Orally Available and Subtype Selective $GAGA_A$ Receptor Modulators*, 14 Molecular Pharmaceutics 2088-2098 (2017).
Forkuo et al., *Development of $GABA_A$ Receptor Subtype-Selective Imidazobenzodiazepines as Novel Asthma Treatments*, 13 Molecular Pharmaceutics 2026-2038 (2016).
Int'l Search Report and Written Opinion in Int'l Application No. PCT/US18/38428 (dated Sep. 7, 2018).
Kaufman et al., *Glutamate decarboxylases and autoimmunity in insulin-dependent diabetes*, 14(4) Trends in Pharmacological Sciences 107-109 (1993).
Lüddens et al., *$GABA_A$/Benzodiazepine Receptor Heterogeneity: Neurophysiological Implications*, 34(3) Neuropharmacology 245-254 (1995) (First Page Only).
Macdonald et al., *$GABA_A$ Receptor Channels*, 17 Annu. Rev. Neurosci. 569-602 (1994).
Munro et al., *Comparison of the Novel Subtype-Selective $GABA_A$ Receptor-Positive Allosteric Modulator NS11394 [3'-[5-(1-Hydroxy-1-methyl-ethyl)-benzoimidazol-1-yl]-biphenyl-2-carbonitrile] with Diazepam, Zolpidem, Bretazenil, and Gaboxadol in Rat Models of Inflammatory and Neuropathic Pain*, 327(3) The Journal of Pharmacology and Experimental Therapeutics 969-981 (Jan. 1, 2008).

(Continued)

*Primary Examiner* — Sarah Pihonak
(74) *Attorney, Agent, or Firm* — Panitch Schwarze Belisario & Nadel LLP; Erin M. Dunston

(57) ABSTRACT

Embodiments methods of reducing an inflammatory immune response (e.g., inhibiting a Th1 response) and/or promoting a regulatory immune response (e.g., enhancing Treg(s)) in a mammal are provided where the method methods involve administering to the mammal a GABAA receptor positive allosteric modulator (PAM) in an amount sufficient to reduce an inflammatory immune response and/or to promote a regulatory immune response said mammal. In certain embodiments the PAM is administered in conjunction with a GABA receptor activating ligand (e.g., GABA).

15 Claims, 3 Drawing Sheets

(56) References Cited

OTHER PUBLICATIONS

Nio et al., *Modulation of T lymphocyte function by neuropeptides. Evidence for their role as local immunoregulatory elements*, 150(12) The Journal of Immunology 5281-5288 (Jun. 15, 1993) (Abstract Only).

Olsen et al., *Molecular biology of GABA$_A$ receptors*, 4 The FASEB Journal 1469-1480 (Mar. 1990).

Tlan et al., *Clinically applicable GABA receptor positive allosteric modulators promote beta-cell replication*, 7(374) Scientific Reports 1-7 (Mar. 23, 2017).

Tian et al., *GABA$_A$ receptors medlate inhibition of T cell responses*, 96 Journal of Neuroimmunology 21-28 (1999).

Torcia et al., *Nerve Growth Factor is an Autocrine Survival Factor for Memory B Lymphocytes*, 85 Cell 345-356 (May 3, 1996).

Office Action issued in Japanese Patent Application No. 2019571282 (with English Translation of Examiner's Comments) dated Jul. 11, 2022.

Communication pursuant to Article 94(3) EPC issued in European counterpart application No. 18821455.5-1112 dated Oct. 26, 2023.

Williams et al., *Diazepam is not a direct allosteric modulator of α1-adrenoceptors, but modulates receptor signaling by inhibiting phosphodiesterase-4*, British Pharmacological Society 1-12 (Dec. 4, 2018).

Canadian Office Action in counterpart Canadian Application No. 3,104,810 (mailed on Jan. 16, 2024).

\* cited by examiner

ENHANCING GABA'S ABILITY TO MODULATE IMMUNE RESPONSES

CROSS-REFERENCE TO RELATED APPLICATIONS

This application is a U.S. National Stage Application pursuant to 35 U.S.C. § 371 of International Patent Application PCT/US2018/038428, filed on Jun. 20, 2018, and published as WO 2018/236955 on Dec. 27, 2018, which claims priority to U.S. Provisional Patent Application 62/524,338, filed on Jun. 23, 2017, all of which are incorporated herein by reference in their entireties for all purposes.

STATEMENT OF GOVERNMENTAL SUPPORT

This invention was made with Government support under DK092480, awarded by the National Institutes of Health. The Government has certain rights in the invention.

BACKGROUND

Many of the cells of the immune system express receptors for neuroactive molecules that modulate immune system function, creating a link between the nervous and immune systems (see, e.g., Nio et al. (1993) *J Immunol.* 150: 5281-5288; Torcia et al. (1996) *Cell*, 85: 345-356).

Gamma-aminobutyric acid (GABA) is a ubiquitous inhibitory neurotransmitter in the central nervous system (see, e.g., Erdo and Wolff (1990) *J. Neurochem*, 54: 363-372; Olsen and Tobin (1990) *Faseb J.* 4: 1469-1480; Kaufman and Tobin (1993) *Trends Pharmacol. Sci.* 14: 107-109; Macdonald and Olsen (1994) *Ann. Rev. Neurosci.*, 17:569-602; and Luddens et al. (1995) *Neuropharmacol.*, 34: 245-254). GABA is synthesized from glutamic acid by the enzyme glutamate decarboxylase (GAD) (see, e.g., Erlander et al. (1991) *Neuron*, 7: 91-100). Outside of the brain, GAD and GABA receptors have been reported in the pancreatic islets, the gastrointestinal tract, ovaries, and adrenal medulla (see, e.g., Erdo and Wolff (1990), supra).

There are at least two types of neuronal GABA receptors, $GABA_A$, and $GABA_B$. $GABA_A$ receptors are ligand-gated ion channels that respond to GABA by opening their integral $Cl^-$ channel (see, e.g., Olsen and Tobin (1990) supra; Macdonald and Olsen (1994) supra; Luddens et al. (1995) supra). Pharmacologically, muscimol acts as an agonist for $GABA_A$ receptors and anxiolytic benzodiazepines as well as anesthetic agents (such as pentobarbital) potentiate the opening of the $GABA_A$-$Cl^-$ channel. Bicuculline and RU5315 antagonize $GABA_A$ receptor function and picrotoxin blocks the $GABA_A$ receptor $Cl^-$ channel (see, e.g., Macdonald and Olsen (1994) supra; and Luddens et al. (1995) supra).

In contrast, $GABA_B$ receptors are coupled to $Ca^{2+}$ or $K^+$ channels via GTP-binding proteins and are selectively activated by baclofen (see, e.g., BoWery (1993) *Annu. Rev. Pharmacol. Taxicol.* 33: 109-147). GABAB receptors are insensitive to bicuculline and picrotoxin.

The administration of GABA or its agonists peripherally inhibits antibody production and modulates macrophage phagocytosis in vivo.

Many diseases, including allergies and autoimmune diseases, as well as graft rejection, result from a deleterious immune response. For example, more than 30 autoimmune diseases are presently known. These include many that have received much public attention, including type 1 diabetes, Rheumatoid arthritis (RA), myasthenia gravis (MG) and multiple sclerosis (MS). Characteristic of these diseases is the attack by the immune system on the tissues of the victim—these tissue antigens being non-immunogenic in non-diseased individuals because of their tolerance of the immune system to "self." In autoimmune diseases, this tolerance apparently is compromised, and the tissue of the afflicted subject is treated as an invader—i.e., the immune system sets about destroying this presumed foreign target. Furthermore, graft rejection results from the activation of T lymphocytes and allergic reaction which are also due to an exacerbated immune response. Alternatively, enhancing immune responses is useful for treating a number of diseases and infections. In addition, redirecting the immune response can result in a more efficient immunity against certain diseases. For example, a viral infection will be more efficiently eliminated if the immune response can be redirected from a predominantly antibody response to a cytotoxic CD8+ T cell-mediated response.

SUMMARY

It was discovered that GABA can inhibit autoimmune responses in different models of T cell-mediated autoimmune diseases, enhance Treg responses, inhibit mouse and human beta-cell apoptosis and promote beta-cell replication. Extending these findings, it was discovered that activation of both $GABA_A$-receptors ($GABA_A$-Rs) and $GABA_B$-Rs can promote mouse beta-cell replication and human beta-cell replication as well. GABA however, has a relatively low affinity for its receptors, a fast off-rate and a short half-life in vivo, which may necessitate that patients take several grams of GABA a few times a day, for therapeutic efficacy, which is somewhat cumbersome and reduces patient compliance.

It was a surprising discovery that GABA receptor activating ligands (agonists) in combination with $GABA_A$-R positive allosteric modulators (PAMS) can promote the replication, and/or survival, and/or function (e.g., insulin production, sensitivity to blood sugar, etc.) of beta cells in mammal. Moreover, it was particularly surprising that the combination of a GABA receptor activating ligand and a PAM is synergistic in these effects on beta cells.

Accordingly, various embodiments contemplated herein may include, but need not be limited to, one or more of the following:

Embodiment 1

A method of reducing an inflammatory immune response and/or promoting a regulatory immune response in a mammal, said method comprising administering to said mammal a $GABA_A$ receptor positive allosteric modulator (PAM) in an amount sufficient to reduce an inflammatory immune response and/or to promote a regulatory immune response said mammal. According to an aspect, embodiment 1 also encompasses a $GABA_A$ receptor positive allosteric modulator (PAM) for use in reducing an inflammatory immune response and/or promoting a regulatory immune response in a mammal. According to another aspect, embodiment 1 further includes the use of a $GABA_A$ receptor positive allosteric modulator (PAM) for preparing a medicament for reducing an inflammatory immune response and/or promoting a regulatory immune response in a mammal. The same aspects as applied to Embodiment 1 also apply to each of embodiments 2 to 64, which are described below.

Embodiment 2

The method of embodiment 1, wherein said PAM reduces an inflammatory immune response.

Embodiment 3

The method according to any one of embodiments 1-2, wherein said inflammatory immune response comprises T cell proliferation.

Embodiment 4

The method according to any one of embodiments 1-3, wherein said PAM promotes a regulatory immune response.

Embodiment 5

The method according to any one of embodiment 1-4, wherein said regulatory immune response comprises an inhibition of a Th1-mediated immune response.

Embodiment 6

The method according to any one of embodiment 1-5, wherein said reduction in an inflammatory immune response or promotion of a regulatory immune response comprises a downregulation of one or more inflammatory cytokines or chemokines.

Embodiment 7

The method of embodiment 6, wherein said reduction in an inflammatory immune response or promotion of a regulatory immune response comprises a downregulation of one or more inflammatory cytokines or chemokines selected from the group consisting of IL-1, IL-12, IL-6, tumor necrosis factor (TNF), interferon gamma (IFN-γ), granulocyte-macrophage colony stimulating factor (GMCSF), and IL-23.

Embodiment 8

The method of embodiment 7, wherein said reduction in an inflammatory immune response or promotion of a regulatory immune response comprises a downregulation IL-1.

Embodiment 9

The method according to any one of embodiments 7-8, wherein said reduction in an inflammatory immune response or promotion of a regulatory immune response comprises a downregulation of IL-12.

Embodiment 10

The method according to any one of embodiments 7-9, wherein said reduction in an inflammatory immune response or promotion of a regulatory immune response comprises a downregulation of IL-6.

Embodiment 11

The method according to any one of embodiments 7-10, wherein said reduction in an inflammatory immune response or promotion of a regulatory immune response comprises a downregulation of tumor necrosis factor (TNF).

Embodiment 12

The method according to any one of embodiments 7-11, wherein said reduction in an inflammatory immune response or promotion of a regulatory immune response comprises a downregulation of interferon gamma (IFN-γ).

Embodiment 13

The method according to any one of embodiments 7-12, wherein said reduction in an inflammatory immune response or promotion of a regulatory immune response comprises a downregulation of granulocyte-macrophage colony stimulating factor (GMCSF), and IL-23.

Embodiment 14

The method according to any one of embodiments 7-13, wherein said reduction in an inflammatory immune response or promotion of a regulatory immune response comprises a downregulation of IL-23.

Embodiment 15

The method according to any one of embodiments 1-14, wherein said reduction in an inflammatory immune response or promotion of a regulatory immune response comprises a reduction of one or more inflammation-related T-cell types.

Embodiment 16

The method of embodiment 15, wherein said reduction of one or more inflammation-related T-cell types comprises a reduction of CD8+ T cells.

Embodiment 17

The method according to any one of embodiments 15-16, wherein said reduction of one or more inflammation-related T-cell types comprises a reduction of T helper 17 ($T_h17$) cells.

Embodiment 18

The method according to any one of embodiments 1-17, wherein said reduction in an inflammatory immune response or promotion of a regulatory immune response comprises an increase in regulatory T cells (Tregs).

Embodiment 19

The method according to any one of embodiments 1-18, wherein said $GABA_A$ receptor positive allosteric modulator (PAM) is administered in conjunction with a GABA receptor activating ligand.

Embodiment 20

The method of embodiment 19, wherein the combination of PAM and GABA receptor activating ligand is more effective to reduce an inflammatory immune response and/or to promote a regulatory immune response in said mammal than when either agent is administered alone.

Embodiment 21

The method of embodiment 20, wherein the combination of PAM and GABA receptor activating ligand is at least 10%, or at least 20%, or at least 30%, or at least 40%, or at least 50%, or at least 60%, or at least 70%, or at least 80%, or at least 90%, or at least 100%, or at least 1.2 fold, or at least 1.5 fold, or at least 2 fold, or at least 3 fold, or at least 4 fold, or at least 5 fold, or at least 10 fold is more effective to reduce an inflammatory immune response and/or to promote a regulatory immune response than when either agent is administered alone.

Embodiment 22

The method of embodiment 19, wherein the GABA receptor activating ligand is used at a lower dosage than would be used to achieve the same reduction of an inflammatory immune response and/or to promotion of a regulatory immune response when used alone and/or said positive allosteric modulator is used at a lower dosage than would be used to achieve the activity for which the PAM is designed and/or approved if the PAM were used alone.

Embodiment 23

The method of embodiment 22, wherein the GABA receptor activating ligand used at less than about 95%, or less than about 90%, or less than about 80%, or less than about 70%, or less than about 60%, or less than about 50%, or less than about 40%, or less than about 30%, or less than about 20%, or less than about 10% of the dosage that would be used to achieve the same effect on reduction of an inflammatory immune response and/or to promotion of a regulatory immune response when the GABA receptor activating ligand is used alone.

Embodiment 24

The method according to any one of embodiments 22-23, wherein said positive allosteric modulator is used at less than about 95%, or less than about 90%, or less than about 80%, or less than about 70%, or less than about 60%, or less than about 50%, or less than about 40%, or less than about 30%, or less than about 20%, or less than about 10% of the dosage that that would be used to achieve the activity for which the PAM is designed and/or approved if the PAM were used alone.

Embodiment 25

The method according to any one of embodiments 22-24, where the GABA receptor activating ligand is used at a lower dosage than would be used to achieve the same effect on reduction of an inflammatory immune response and/or to promotion of a regulatory immune response when used alone and/or said positive allosteric modulator is used at a subtherapeutic dosage.

Embodiment 26

The method according to any one of embodiments 1-25, wherein said mammal is a human.

Embodiment 27

The method of embodiment 26, wherein said mammal is a human diagnosed with type I diabetes.

Embodiment 28

The method of embodiment 26, wherein said mammal is diagnosed as pre-diabetic.

Embodiment 29

The method according to any one of embodiments 1-28, wherein said mammal is a non-human mammal.

Embodiment 30

The method according to any one of embodiments 1-29, wherein said GABA receptor activating ligand and said PAM act synergistically to reduce an inflammatory immune response and/or to promote a regulatory immune response.

Embodiment 31

The method according to any one of embodiments 1-30, wherein said PAM comprises an agent selected from the group consisting of a barbituate, a benzodiazepine, a quinazolinone, and a neurosteroid.

Embodiment 32

The method of embodiment 31, wherein said PAM comprises a barbituate.

Embodiment 33

The method of embodiment 32, wherein said PAM comprises a barbiturate selected from the group consisting of allobarbital (5,5-diallylbarbiturate), amobarbital (5-ethyl-5-isopentyl-barbiturate), aprobarbital (5-allyl-5-isopropyl-barbiturate), aiphenal (5-allyl-5-phenyl-barbiturate), barbital (5,5-diethylbarbiturate), brallobarbital (5-allyl-5-(2-bromo-allyl)-barbiturate), pentobarbital (5-ethyl-5-(1-methyl-butyl)-barbiturate), phenobarbital (5-ethyl-5-phenylbarbiturate), secobarbital (5-[(2R)-pentan-2-yl]-5-prop-2-enyl-barbiturate).

Embodiment 34

The method of embodiment 31, wherein said PAM comprises a benzodiazepine.

Embodiment 35

The method of embodiment 34, wherein said PAM comprises a benzodiazepine selected from the group consisting of alprazolam, bromazepam, chlordiazepoxide, midazolam, clonazepam, clorazepate, diazepam, estazolam, flurazepam, halazepam, ketazolam, lorazepam, nitrazepam, oxazepam, prazepam, quazepam, temazepam, and triazolam.

Embodiment 36

The method of embodiment 34, wherein said PAM comprises alprazolam.

Embodiment 37

The method of embodiment 36, wherein said alprazolam is administered at a dosage less than that used to treat used to treat an anxiety disorder, a panic disorder, and/or anxiety caused by depression.

Embodiment 38

The method of embodiment 36, wherein said alprazolam is administered as an immediate release tablet less than 1.5 mg orally per day or less than 1.0 mg orally per day, or less than 0.5 mg orally per day, or as an extended release tablet less than 0.5 mg orally per day, or less than about 0.4 mg orally per day or less than about 3 mg orally per day.

Embodiment 39

The method of embodiment 34, wherein said PAM comprises midazolam.

Embodiment 40

The method of embodiment 39, wherein said midazolam is administered at a dosage less than that used to reduce anxiety, or producing drowsiness or anesthesia before medical procedures or surgery, or to maintain sedation or anesthesia.

Embodiment 41

The method of embodiment 39, wherein said midazolam is administered at a dosage less than 1 mg IV, or less than about 0.8 mg IV, or less than about 0.5 mg IV, or less than about 0.01 mg/kg IV, or less than about 0.07 mg/kg IM, or less than about 0.05 mg/kg IM, or less than about 0.03 mg/kg IM, or less than about 0.01 mg/kg.

Embodiment 42

The method of embodiment 34, wherein said PAM comprises clonazepam.

Embodiment 43

The method of embodiment 42, wherein said clonazepam is administered at a dosage less than that used to treat seizure disorders (including absence seizures or Lennox-Gastaut syndrome), or less than that used to treat panic disorder (including agoraphobia) in adults.

Embodiment 44

The method of embodiment 42, wherein said clonazepam is administered at a dosage less than about 0.5 mg orally per day, or less than about 0.25 mg orally per day, or less than bout 0.01 mg/kg/day, or less than about 0.005 mg/kg/day.

Embodiment 45

The method of embodiment 31, wherein said PAM comprises a neurosteroid.

Embodiment 46

The method of embodiment 45, wherein said PAM comprises a neurosteroid selected from the group consisting of allopregnanolone (3α-hydroxy-5α-pregnan-20-one), and pregnanolone.

Embodiment 47

The method according to any one of embodiments 1-30, wherein said PAM comprises an agent selected from the group consisting of Algiax APB, Algiax Ap4, Algiax AP325, and Algiax AP3.

Embodiment 48

The method of embodiment 47, wherein said PAM comprises AP325.

Embodiment 49

The method of embodiment 48, wherein said AP325 is administered at a dosage lower than that used for neuropathic pain or spinal cord injury.

Embodiment 50

The method according to any one of embodiments 19-49, wherein said GABA receptor activating ligand comprises GABA.

Embodiment 51

The method according to any one of embodiments 19-49, wherein said GABA receptor activating ligand comprises an agent selected from the group consisting of homotaurine, bamaluzole, gabamide, GABOB, gaboxadol, ibotenic acid, isoguvacine, trans-aminocyclopentane-3-carboxylic acid, trans-amino-4-crotonic acid, THIP, imidazole acetic acid, β-guanidino-propionic acid, homohypotaurine, 3-aminopropanesulfonic acid, kojic amine, cis-3-[(aminoiminomethyl)thio]propenoic acid, homo-β-proline, isonipecotic acid, muscimol, phenibut, picamilon, progabide, quisqualamine, progabide acid (SL 75102), thiomuscimol, pregabalin, vigabatrin, 6-aminonicotinic acid, XP13512, and ((±)-1-([(α-isobutanoyloxyethoxy) carbonyl] aminomethyl)-1-cyclohexane acetic acid).

Embodiment 52

The method according to any one of embodiments 19-51, wherein said GABA receptor activating ligand is not an alcohol.

Embodiment 53

The method according to any one of embodiments 19-52, wherein said GABA receptor activating ligand is not a kavalactone.

Embodiment 54

The method according to any one of embodiments 19-53, wherein said GABA receptor activating ligand is not skullcap or a skullcap constituent.

Embodiment 55

The method according to any one of embodiments 19-54, wherein said GABA receptor activating ligand is not valerian or a valerian constituent.

Embodiment 56

The method according to any one of embodiments 19-55, wherein said GABA receptor activating ligand is not a volatile gas.

Embodiment 57

The method according to any one of embodiments 1-56, wherein said method is used to treat an inflammatory disease.

Embodiment 58

The method of embodiment 57, wherein said method is used to treat an inflammatory disease selected from the group consisting of metabolic syndrome, and autoimmune disease such as type I diabetes (T1D), rheumatoid arthritis, systemic lupus erythematosus, myasthenia gravis, and multiple sclerosis.

Embodiment 59

The method according to any one of embodiments 1-56, wherein said method is used to prevent or lessen graft rejection in a subject receiving a tissue graft.

Embodiment 60

The method according to any one of embodiments 1-56, wherein said method is used to reduce an allergic response.

Embodiment 61

The method of embodiment 60, wherein said method is used to reduce and allergic response in a condition selected from the group consisting of hay fever, extrinsic asthma, insect bite and sting allergy, food and drug allergy, allergic rhinitis, bronchial asthma, anaphylactic syndrome, urticaria, angioedema, atopic dermatitis, allergic contact dermatitis, erythema nodosum, erythema multiforme, Stevens-Johnson Syndrome, cutaneous necrotizing venulitis, and bullous skin disease.

Embodiment 62

The method according to any one of embodiments 1-61, wherein said mammal is not under treatment for one or more conditions selected from the group consisting of neuropathic pain, spinal cord injury, an anxiety disorder, a panic disorder, anxiety caused by depression, a seizure disorder (including absence seizures or Lennox-Gastaut syndrome), and catamenial epilepsy.

Embodiment 63

The method according to any one of embodiments 1-62, wherein said PAM is not administered to produce drowsiness or anesthesia before a medical procedure or surgery, or to maintain sedation or anesthesia.

Embodiment 64

The method according to any one of embodiments 1-63, wherein said PAMS that are BBB-permeable are administered at doses below those used for CNS indications.

Definitions

The term "GABA receptor activating ligand" refers to an agent that is an agonist for one or more of the GABA receptors. In certain embodiments, the GABA receptor activating ligand is an agonist for at least the $GABA_A$ receptor.

The terms "positive allosteric modulator of the $GABA_A$ receptor" or (PAM) refers to a molecule that increases the activity of the $GABA_A$ receptor protein in the vertebrate central nervous system. Unlike $GABA_A$ receptor agonists, $GABA_A$ PAMs do not bind at the same active site as the gamma-aminobutyric acid (GABA) neurotransmitter molecule. In various embodiments, the PAMs trigger or potentiate the $GABA_A$ receptor to open its chloride channel.

The term "subtherapeutic dosage" when used with respect to a PAM refers to a dosage below the approved and/or recommended and/or recognized dosage of the PAM when used for the activity for which the PAM was originally designed and/or approved. Thus, for example, the subtherapeutic dosage of a benzodiazepine such as alprazolam refers to a dosage below the approved and/or recommended and/or recognized dosage of that benzodiazepine for depression, panic disorder, and/or anxiety. In certain embodiments the subtherapeutic dosage is less than 90% or less than about 80%, or less than about 70%, or less than about 60%, or less than about 50%, or less than about 40%, or less than about 30%, or less than about 20%, or less than about 10% of the recommended dosage for the activity for which the PAM was designed and/or approved (e.g., depression, panic disorder, seizures, and/or anxiety).

The phrases "in conjunction with" or "in combination with" when used in reference to the use of the active agent(s) described herein (e.g., one or more GABA receptor activating ligand(s)) in conjunction with one or more other drugs described herein (e.g., one or more PAMs) indicates that the GABA receptor activating ligand(s) and the PAM(s) are administered so that there is at least some chronological overlap in their physiological activity on the organism, and in particular on beta cells. Thus, in various embodiments, the GABA receptor activating ligand (s) and PAM(s) can be administered simultaneously and/or sequentially. In sequential administration there may even be some substantial delay (e.g., minutes or even hours or days) before administration of the second moiety as long as the first administered drug/agent has exerted some physiological alteration on the organism when the second administered agent is administered or becomes active in the organism.

The term "regulatory response" includes the action of regulatory T cells and B cells, antigen presenting cells, and other cells of the innate immune system (as well as their precursor cells) and their secreted anti-inflammatory cytokines, such as TGF-β, IL-10, IL-4, IL-13, IL-27, IL-35, IL-2, Granzyme B, and indoleamine 2,3-dioxygenase.

3H-thymidine uptake, as expressed in cpm (counts per minute). Abscissa: alprazolam (Xanax) concentrations as expressed, in M.

Figure 3:
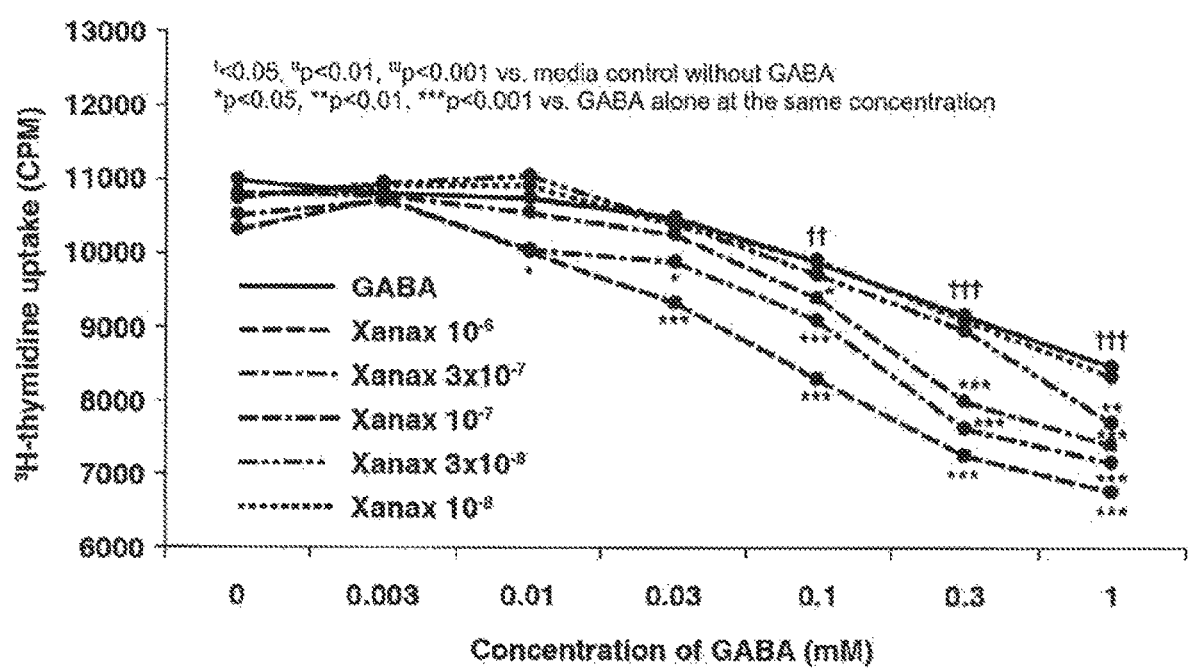

FIG. 3 shows that the combination of GABA and alprazolam (Xanax) more effectively inhibits immune cell proliferation (inflammatory response) in response to HEL. At the starting point with GABA in the absence of Xanax (labeled "0" on the abscissa axis), the curves from top to bottom represent: (i) without Xanax, (ii) Xanax $10^{-6}$, (iii) Xanax $3\times10^{-7}$, (iv) Xanax $10^{-7}$, (v) Xanax $3\times10^{-8}$ and (vi) Xanax $10^{-8}$. Ordinate: 3H-thymidine uptake, as expressed in cpm (counts per minute). Abscissa: GABA concentrations, as expressed in mM.

DETAILED DESCRIPTION

The compositions, methods and uses described herein pertain to the discovery that PAM(s) (positive allosteric modulator(s) of GABA receptors (e.g., $GABA_A$ receptors)) can reduce an inflammatory immune response and/or promote a regulatory immune response in a mammal. Moreover, it was also discovered that the use of the PAM(s) in combination with one or more GABA receptor activating ligand(s) provides a significantly greater effect than the PAM(s) or GABA receptor activating ligand(s) used alone. Without being bound to a particular theory it appears that the combination of a GABA receptor activating ligand and a PAM has a synergistic effect on the reduction of an inflammatory immune response and/or the promotion of a regulatory immune response.

Accordingly it is believed that in certain embodiments the presence of a GABA-R agonist, particularly in the presence of a small amount of exogenous GABA, a GABA-R PAM can effectively reduce immune inflammatory responses (e.g., inhibit a Th1 response) and/or promote an regulatory immune response (e.g., promote regulatory T cells (Tregs)). Accordingly, in certain embodiments, a method of reducing an inflammatory immune response and/or promoting a regulatory immune response in a mammal is provided where the method comprises administering to the mammal a $GABA_A$ receptor positive allosteric modulator (PAM) in an amount sufficient to reduce an inflammatory immune response and/or to promote a regulatory immune response in the mammal. In certain embodiments the PAM is administered on conjunction with a GABA receptor activating ligand. According to those embodiments, it is provided a $GABA_A$ receptor positive allosteric modulator (PAM) for use for reducing an inflammatory immune response and/or promoting a regulatory immune response in a mammal. Still according to those embodiments, it is provided the use of a $GABA_A$ receptor positive allosteric modulator (PAM) for preparing a medicament for reducing an inflammatory immune response and/or promoting a regulatory immune response in a mammal.

Without being bound to a particular theory, it is believed that one important outcome is that that the combination treatment can modulate immune responses using lower dosages of either a GABA-R agonist (e.g., GABA), the PAM or both, thereby making treatment easier (e.g., avoiding large consumption of GABA), more effective, and potentially safer.

Accordingly, in various embodiments, methods of reducing an inflammatory immune response and/or promoting a regulatory immune response in mammal are provided where the methods involve administering to a mammal in need thereof one or more PAM(s) in conjunction with a GABA receptor activating ligand where the GABA receptor activating ligand is used at a lower dosage than would be used to reduce an inflammatory immune response and/or promote a regulatory immune response than when used alone and/or the positive allosteric modulator is used at a subtherapeutic dosage. In certain embodiments the administration of both agents reduces an inflammatory immune response. In certain embodiments the administration of both agents promotes a regulatory immune response.

In certain embodiments pharmaceutical formulations are provided that comprise a GABA receptor activating ligand and a $GABA_A$ receptor positive allosteric modulator (PAM). In certain embodiments kits for the practice of the methods described herein are also contemplated. In various embodiments such kits comprises a container containing a GABA receptor activating ligand and a container containing a $GABA_A$ receptor positive allosteric modulator (PAM), and optionally instructional materials teaching, inter alia, the use of these agents in the methods described herein.

Uses of PAM(s), Optionally in Combination with One or More GABA Receptor Activating Ligand(s)

The PAM(s) described herein, optionally in combination with one or more GABA receptor activating ligand(s) can be used to treat a number of diseases involving immune function. More specifically the compounds or combinations thereof can be used to treat conditions in which downregulation of an inflammatory response (e.g., Th1 inhibition) and/or the promotion (upregulation) of a regulatory immune response (e.g., Treg response) is desirable.

In certain embodiments the compounds are administered peripherally (e.g., by oral, transdermal, intravenous, subcutaneous administration or by using a pump). In certain embodiments, the compounds are unable to cross the blood-brain barrier and, therefore, do not affect the central nervous system.

Inflammatory and/or Autoimmune Diseases

The PAM(s) described herein, alone or in combination with one or more GABA receptor activating ligand(s), be used to reduce inflammation (e.g., to inhibit a Th1 response) and/or to enhance Treg responses. In certain embodiments the reduction of inflammation is characterized by the reduction of one or more inflammatory (e.g., proinflammatory) cytokines or chemokines and/or the reduction of one or more inflammation-related T-cell types. Thus, for example, in certain embodiments the reduction of inflammation is characterized by a reduction in one or more inflammatory cytokines or chemokines such as interleukin-1 (IL-1), interleukin-12 (IL-12), interleukin-6 (IL-6), tumor necrosis factor (TNF), interferon gamma (IFN-γ), granulocyte-macrophage colony stimulating factor (GMCSF), interleukin-17 (IL-17), interleukin-23 (IL-23), and the like. In certain embodiments the reduction in inflammation is characterized by a reduction of one or more inflammation-related T-cell types such as CD8+ T cells, T helper 17 ($T_h17$) cells, and the like.

It is believed that such actions are highly beneficial when treating inflammatory disease that include, but are not limited to metabolic syndrome, and autoimmune disease such as type I diabetes (T1D), rheumatoid arthritis, systemic lupus erythematosus, myasthenia gravis, and multiple sclerosis, and the like.

Graft Rejection

It has been shown that agents that block the ability of T cells to mount an immune response in humans effectively prevent or lessen graft rejection. In addition, studies of the process of graft rejection have shown that it at least in part, due to antigen-specific activation of T lymphocytes, especially those bearing CD8 surface molecules. Inhibiting the T cell-mediated immune response therefore leads to greater tolerance of grafts.

Accordingly in certain embodiments, the PAM(s) described herein, alone or in combination with one or more GABA receptor activating ligand(s) are used to inhibit T cell-mediated inflammatory immune responses and thereby promote greater tolerance of grafts (e.g., to increase graft survival). Such grafts can include, but are not limited to beta cell transplants, and the like.

Allergy

A wide variety of atopic or allergic disorders, commonly known as asthma or allergies, result from the effects of activating T cells. Such allergic disorders include, e.g., hay fever, extrinsic asthma, insect bite and sting allergies, food and drug allergies, allergic rhinitis, bronchial asthma, anaphylactic syndrome, urticaria, angioedema, atopic dermatitis, allergic contact dermatitis, erythema nodosum, erythema multiforme, Stevens-Johnson Syndrome, cutaneous necrotizing venulitis, bullous skin diseases, and the like. Without being bound to a particular theory, it is believe the methods described herein (e.g., administration of one or more PAM(s) alone, or in combination with one or more GABA receptor activating ligand(s)) can be used in an intervention to reduce allergic reactions in these and other conditions.

Inhibition Th1 Cell-mediated Immune Responses

As noted above, the PAM(s) described herein, alone or in combination with one or more GABA receptor activating ligand(s) can be used to inhibit Th1-mediated immune responses. Th1 cells produce IL-2, and gamma-interferon (γ-IFN), and mediate helper cell functions associated with cytotoxic T lymphocytes (CTLs), delayed-type hypersensitivity (DTH) and macrophage activation. IL-2 produced by Th1 cells plays a major role in the activation and differentiation of CTL precursors into mature CTL effectors. Th1 cells are involved in what is called "cell-mediated" immunity, which usually deals with infections by viruses and certain bacteria. They are the body's first line of defense against pathogens that gets inside our cells. However Th1 cells tend to be pro-inflammatory and are involved in the development of autoimmune diseases.

The methods described herein can be used to inhibit Th-1 cell-mediated immunity and/or to promote a regulatory response (e.g., enhance Tregs) and are believed to be of use in the treatment of pathologies including, but not limited to autoimmune conditions such as Type I diabetes, Multiple sclerosis, myasthenia, gravis, Hashimoto's Thyroiditis, Grave's Disease, Crohn's Disease, Psoriasis, Sjoren's Syndrome, Celiac Disease, Rheumatoid Arthritis, and the like. The foregoing uses are illustrative and non-limiting. Using the teachings provided herein numerous other applications of the described methods will be available to one of skill in the art.

GABA$_A$ Receptor Positive Allosteric Modulators (PAMs)

Positive allosteric modulators (PAMs) of GABAA receptors are well known to those of skill in the art. Illustrative PAMS include, but are not limited to alcohols (e.g., ethanol, isopropanol), avermectins (e.g., ivermectin), barbiturates (e.g., phenobarbital), benzodiazepines, bromides (e.g., potassium bromide, carbamates (e.g., meprobamate, carisoprodol), chloralose, chlormezanone, clomethiazole, dihydroergolines (e.g., ergoloid (dihydroergotoxine)), etazepine, etifoxine, imidazoles (e.g., etomidate), kavalactones (found in kava), loreclezole, neuroactive steroids (e.g., allopregnanolone, ganaxolone), nonhenzodiazepines (e.g., zaleplon, zolpidem, zopiclone, eszopiclone), petrichloral, phenols (e.g., propofol), piperidinediones (e.g., glutethimide, methyprylon), propanidid, pyrazolopyridines (e.g., etazolate), quinazolinones (e.g., methaqualone), skullcap constituents (e.g. constituents of Scutellaria sp. including, but not limited to flavonoids such as baicalein), stiripentol, sulfonylalkanes (e.g., sulfonmethane, tetronal, trional), valerian constituents (e.g., valeric acid, valerenic acid), and certain volatiles/gases (e.g., chloral hydrate, chloroform, diethyl ether, sevoflurane). In various embodiments the PAMs used in combination with the GABA receptor activating ligands exclude alcohols, and/or kavalactones, and/or skullcap or skullcap constituents, and/or valerian or valerian constituents, and/or volatile gases.

In certain embodiments the PAM comprises an agent selected from the group consisting of a barbituate, a benzodiazepine, a quinazolinone, and a neurosteroid. One illustrative, but non-limiting quinolone is d (+)-ROD188 ((1R, 2'R)-1-(2,3,4,5-Tetrahydro-5-oxo-2-furyl)-2-N-(p-toluenesulphonyl)-1,2,3,4-tetrahydroisoquinoline, see, e.g., Thomet et al. (2000) Br. J. Pharmacol., 131(4): 843-850). Illustrative barbituates include, but are not limited to allobarbital (5,5-diallylbarbiturate), amobarbital (5-ethyl-5-isopentyl-barbiturate), aprobarbital (5-allyl-5-isopropyl-barbiturate), alphenal (5-allyl-5-phenyl-barbiturate), barbital (5,5-diethylbarbiturate), brallobarbital (5-allyl-5-(2-bromo-allyl)-barbiturate), pentobarbital (5-ethyl-5-(1-methylbutyl)-barbiturate), phenobarbital (5-ethyl-5-phenylbarbiturate), secobarbital (5-[(2R)-pentan-2-yl]-5-prop-2-enyl-barbiturate), and the like.

Illustrative benzodiazepines include, but are not limited to alprazolam, bromazepam, chlordiazepoxide, clonazepam, clorazepate, diazepam, estazolam, flurazepam, halazepam, ketazolam, lorazepam, nitrazepam, oxazepam, prazepam, quazepam, temazepam, triazolam, and the like.

Illustrative neurosteroids include, but are not limited to allopregnanolone, and pregnanolone.

In certain embodiments the PAM of particular use comprises alprazolam (XANAX®).

Other suitable PAMs include, but are not limited to the PAMS produced by Algiax (e.g., Algiax AP8, Algiax Ap4, Algiax AP325, and Algiax AP3).

The above-identified PAMs are intended to be illustrative and non-limiting. Other PAMs are known to those of skill in the art and their use in the methods, formulations, and kits described herein is contemplated.

GABA Receptor Activating Ligands

GABA receptor activating ligands are well known to those of skill in the art. Such ligands include for example gamma-aminobutyric acid (GABA) the native ligand for the GABA receptor. Other GABA receptor activating ligands include, but are not limited to homotaurine, bamaluzole, gabamide, GABOB, gaboxadol, ibotenic acid, isoguvacine, trans-aminocyclopentane-3-carboxylic acid, trans-amino-4-crotonic acid, THIP, imidazole acetic acid, β-guanidinopropionic acid, homohypotaurine, 3-aminopropanesulfonic acid, kojic amine, cis-3-[(aminoiminomethyl)thio]propenoic acid, homo-β-proline, isonipecotic acid, muscimol, phenibut, picamilon, progabide, quisqualamine, progabide acid (SL 75102), thiomuscimol, pregabalin, vigabatrin, 6-aminonicotinic acid, XP13512 ((±)-1-([(α-isobutanoyloxyethoxy) carbonyl] aminomethyl)-1-cyclohexane acetic acid), and the like.

These GABA receptor activating ligands are intended to be illustrative and non-limiting. Other GABA receptor activating ligands are known to those of skill in the art and their use in the methods, formulations, and kits described herein is contemplated.

Combined Formulations

In various embodiments pharmaceutical formulations are contemplated that comprise one or more positive allosteric modulators of the $GABA_A$ receptor (PAM(s)) and one or more GABA receptor activating ligands. In certain embodiments the GABA receptor activating ligand is present at a lower unit dosage than in a therapeutic formulation comprising a GABA receptor activating ligand alone and/or the PAM is at a lower unit dosage than in a typical, and/or approved, and/or recommended therapeutic formulation comprising the PAM alone.

In certain embodiments the PAM in the combined formulation comprises one or more of an alcohol (e.g., ethanol, isopropanol), avermectins (e.g., ivermectin), barbiturates (e.g., phenobarbital), benzodiazepines, bromides (e.g., potassium bromide, carbamates (e.g., meprobamate, carisoprodol), chloralose, chlormezanone, clomethiazole, dihydroergolines (e.g., ergoloid (dihydroergotoxine)), etazepine, etifoxine, imidazoles (e.g., etomidate), kavalactones (found in kava), loreclezole, neuroactive steroids (e.g., allopregnanolone, ganaxolone), nonbenzodiazepines (e.g., zaleplon, zolpidern, zopiclone, eszopiclone), petrichloral, phenols (e.g., propofol), piperidinediones (e.g., glutethimide, methyprylon), propanidid, pyrazolopyridines (e.g., etazolate), quinazolinones (e.g., methaqualone), skullcap constituents (e.g. constituents of Scutellaria sp. including, but not limited to flavonoids such as baicalein), stiripentol, sulfonylalkanes (e.g., sulfonmethane, tetronal, trional), valerian constituents (e.g., valeric acid, valerenic acid). In various embodiments the PAMs used in combination with the GABA receptor activating ligands exclude alcohols, and/or kavalactones, skullcap or skullcap constituents, and the like, e.g., as described herein.

In certain embodiments the GABA receptor ligand in the combined formulation comprises one or more of gamma-aminobutyric acid (GABA), homotaurine, bamaluzole, gabamide, GABOB, gaboxadol, ibotenic acid, isoguvacine, isonipecotic acid, muscimol, phenibut, picamilon, progabide, quisqualamine, progabide acid (SL 75102), thiomuscimol, pregabalin, vigabatrin, 6-aminonicotinic acid, XP13512 ((±)-1-([(α-isobutanoyloxyethoxy) carbonyl] aminomethyl)-1-cyclohexane acetic acid), and the like, e.g., as described herein.

In certain embodiments the combined formulation comprises GABA and alprazolam.

The active agent(s) (e.g., PAM(s) and GABA receptor activating ligand(s) described herein) can be formulated and administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience, and as described above.

For example, a pharmaceutically acceptable salt can be prepared for any of the agent(s) described herein (e.g., GABA receptor activating ligand(s) and PAM(s) described herein) having a functionality capable of forming a salt. A pharmaceutically acceptable salt is any salt that retains the activity of the parent compound and does not impart any deleterious or untoward effect on the subject to which it is administered and in the context in which it is administered.

In various embodiments pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically active agents as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the active agents identified herein (e.g., combined GABA receptor activating ligand(s) and PAM(s)) are useful for parenteral administration, topical administration, oral administration, nasal administration (or otherwise inhaled), rectal administration, or local administration, such as by aerosol or transdermally, for reducing an inflammatory immune response and/or promoting a regulatory immune response in a mammal.

In various embodiments the active agents described herein can also be combined with a pharmaceutically acceptable carrier(s) (excipient(s)) to form a pharmacological composition containing both agents. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disintegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., alaproclate and other compounds described herein, or a tautomer(s) or stereoisomer(s) thereof, or pharmaceutically acceptable salts or solvates of said alaproclate and other compounds, said stereoisomer(s), or said tautomer(s), or analogues, derivatives, or prodrugs thereof) and the resulting composition is compressed. Where necessary the compressed product is coated, e.g., using known methods for masking the taste or for enteric dissolution or sustained release. Suitable coating materials include, but are not limited to ethyl-cellulose, hydroxymethylcellulose, POLYOX® yethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physiochemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, mucoadherent films, topical varnishes, lipid complexes, etc.

Pharmaceutical compositions comprising the active agents described herein (e.g., GABA receptor activating ligand(s) and PAM(s)) can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the active agent(s) into preparations that can be used pharmaceutically. Proper formulation is dependent upon the route of administration chosen.

In certain embodiments, the combined active agents (e.g., GABA receptor activating ligand(s) and PAM(s)) are formulated for oral administration. Suitable formulations or oral administration can be readily prepared by combining the active agent(s) with pharmaceutically acceptable carriers suitable for oral delivery well known in the art. Such carriers enable the active agent(s) described herein to be formulated as tablets, pills, dragees, caplets, lizenges, gelcaps, capsules, liquids, gels, syrups, slurries, suspensions and the like, for oral ingestion by a patient to be treated. For oral solid formulations such as, for example, powders, capsules and tablets, suitable excipients can include fillers such as sugars (e.g., lactose, sucrose, mannitol and sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose), synthetic polymers (e.g., polyvinylpyrrolidone (PVP)), granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. The preparation of enteric-coated particles is disclosed for example in U.S. Pat. Nos. 4,786,505 and 4,853,230.

For administration by inhalation, the active agent(s) (e.g., GABA receptor activating ligand(s) and PAM(s) described herein) are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g.

gelatin for use in an inhaler or insufflator may be formulated containing a powder mix of the compound and a suitable powder base such as lactose or starch.

In certain embodiments the active agents described herein are formulated for systemic administration (e.g., as an injectable) in accordance with standard methods well known to those of skill in the art. Systemic formulations include, but are not limited to, those designed for administration by injection, e.g. subcutaneous, intravenous, intramuscular, intrathecal or intraperitoneal injection, as well as those designed for transdermal, transmucosal oral or pulmonary administration. For injection, the active agents described herein can be formulated in aqueous solutions, preferably in physiologically compatible buffers such as Hanks solution, Ringer's solution, or physiological saline buffer and/or in certain emulsion formulations. The solution(s) can contain formulatory agents such as suspending, stabilizing and/or dispersing agents. In certain embodiments the active agent(s) can be provided in powder form for constitution with a suitable vehicle, e.g., sterile pyrogen-free water, before use. For transmucosal administration, and/or for blood/brain barrier passage, penetrants appropriate to the barrier to be permeated can be used in the formulation. Such penetrants are generally known in the art. Injectable formulations and inhalable formulations are generally provided as a sterile or substantially sterile formulation.

In addition to the formulations described previously, the active agents (e.g., GABA receptor activating ligand(s) and PAM(s) described herein) may also be formulated as a depot preparations. Such long acting formulations can be administered by implantation (for example subcutaneously or intramuscularly) or by intramuscular injection. Thus, for example, the active agent(s) may be formulated with suitable polymeric or hydrophobic materials (for example as an emulsion in an acceptable oil) or ion exchange resins, or as sparingly soluble derivatives, for example, as a sparingly soluble salt.

In certain embodiments the active agent(s) described herein can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Alternatively, other pharmaceutical delivery systems can be employed. For example, liposomes, emulsions, and microemulsions/nanoemulsions are well known examples of delivery vehicles that may be used to protect and deliver pharmaceutically active compounds. Certain organic solvents such as dimethylsulfoxide also can be employed, although usually at the cost of greater toxicity.

In certain embodiments the combined formulation comprises the GABA receptor activating ligand(s) and/or the PAM(s) at a lower dosage (unit dosage) than would be provided if the GABA receptor activating ligand and/or the PAM were used alone. In certain embodiments GABA receptor activating ligand is present at less than about 90%, or at less than about 80%, or at less than about 70%, or at less than about 60%, or at less than about 50%, or at less than about 40%, or at less than about 40%, or at less than about 30%, or at less than about 10%, or at less than about 5% of the GABA receptor activating ligand required to reduce an inflammatory immune response and/or to promote a regulatory immune response in a mammal when the GABA receptor activating ligand is used alone.

In certain embodiments the PAM(s) are provided at a subtherapeutic dosage. This refers to a dosage below the approved and/or recommended and/or recognized dosage of the PAM when used for the activity for which the PAM was originally designed and/or approved.

Thus, for example, the recommended/approved dosage of alprazolam (immediate release tablets) for treatment of panic disorder is an initial dose of 0.5 mg orally 3 times a day with a maintenance dose of 1 to 10 mg/day in divided doses and a mean dose of 5 to 6 mg/day in divided doses. The recommended/approved dosage extended release alprazolam tablets is 0.5 mg to 1 mg once a day and the maintenance dose is 1 to 10 mg once a day with a mean dose of 3 to 6 mg once a day. The recommended/approved dosage of alprazolam (immediate release tablets) for treatment of adult depression is an initial dose of 0.5 mg orally 3 times a day which is increased to an average effective dose of 3 mg orally daily in divided, doses. Geriatric doses for anxiety are provided at an initial dose of 0.25 mg orally 2 to 3 times a day in elderly or debilitated patients and a daily dose greater than 2 mg meets the Beers criteria as a medication that is potentially inappropriate for use in older adults.

In a formulation a subtherapeutic dosage is typically less than the lowest recommended/approved unit dosage form, e.g., in the case of alprazolam less than 0.25 mg as a unit dosage form and a total of less than 0.5 mg daily in a treatment method. In certain embodiments the subtherapeutic dosage is less than 90% or less than about 80%, or less than about 70%, or less than about 60%, or less than about 50%, or less than about 40%, or less than about 30%, or less than about 20%, or less than about 10% of this recommended/approved dosage.

These dosages are intended to be illustrative and not limiting. The actual dosage amount of the BABA receptor activating ligand and PAM administered to a subject can be determined by physical and physiological factors such as body weight, severity of condition, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

Kits

In certain embodiments kits are provided for the practice of the methods described herein. In various embodiments the kits comprise a container containing a GABA activating ligand, and a container containing positive allosteric modulator of the $GABA_A$ receptor as described herein. In certain embodiments the kit comprises GABA and alprazolam.

In certain embodiments the GABA receptor activating ligand(s) and PAM(s) can be provided in unit dosage formulation(s) (e.g., tablet, caplet, patch, etc.) and/or may be optionally combined with one or more pharmaceutically acceptable excipients. In certain embodiments the GABA receptor activating ligand(s) and PAM(s) can be provided in separate containers. In certain embodiments the GABA receptor activating ligand(s) and PAM(s) can be provided in the same container. In certain embodiments the GABA receptor activating ligand(s) and PAM(s) can be provided in the same container as a combined formulation.

In addition, the kits optionally include labeling and/or instructional materials providing directions (i.e., protocols) for the practice of the methods of this invention. Certain labeling or instructional materials describe the use of one or more PAM(s) alone or in combination with one or more GABA receptor activating ligand(s) to reduce an inflammatory immune response and/or to promote a regulatory immune response in a mammal. The labeling or instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Use of a PAM, Optionally in Combination with a GABA Receptor Activating Ligand to Suppress an Inflammatory Immune Response and/or to Promote a Regulatory Immune Response GABA-R positive allosteric modulators (PAMs) enhance the action of GABA. They do not bind to the GABA-binding site (i.e., they are not agonists), but rather elsewhere on GABA-Rs. While they do not have agonist function to activate the GABA-R, they potentiate the action of GABA when GABA binds to the receptor. Since the levels of GABA in blood are low, a PAM alone (e.g., in the absence of an exogenous GABA receptor agonist) is unlikely to affect most peripheral immune responses. Consistent with this, it is noted that individuals who take the GABA-R PAM alprazolam (Xanax) long-term are not reported to have immune suppression.

However, GABA is secreted within the islets and it is believed that the administration of a PAM alone may can synergize with the intra-islet GABA to inhibit the inflammatory pathology insulitis. It is also believed that antigen presenting cells can make some GABA, that can synergize with an administered PAM.

In addition to synergy with localized endogenous GABA secretion, it is believed that that in the presence of a small amount of exogenous GABA, a GABA-R PAM can effectively reduce immune inflammatory responses (e.g., inhibit Th1 responses) and/or enhance a regulatory (Treg) response. It is believed the idea to supply exogenous GABA and a PAM in order to modulate immune responses is novel. Moreover, it is that the combination treatment can modulate immune responses using lower dosages of either GABA, the PAM or both, thereby making treatment easier (e.g., avoiding large consumption of GABA), more effective, and potentially safer.

Methods

Mice were injected with hen egg lysozyme (HEL, a prototypic foreign antigen) in 50% complete Freund's adjuvant (CFA) in their hind food-pad. Nine days later, lymph node mononuclear cells were isolated and $3 \times 10^5$ mononuclear cells/well were tested in triplicate in 1% FCS HL-1 medium for T cell recall responses to HEL in the presence of different concentrations of GABA, or the PAM alprazolam (Xanax). During the last 16 h of a 96 h incubation period, 1 mCi $^3$H thymidine was added into each well.

Figure 1:
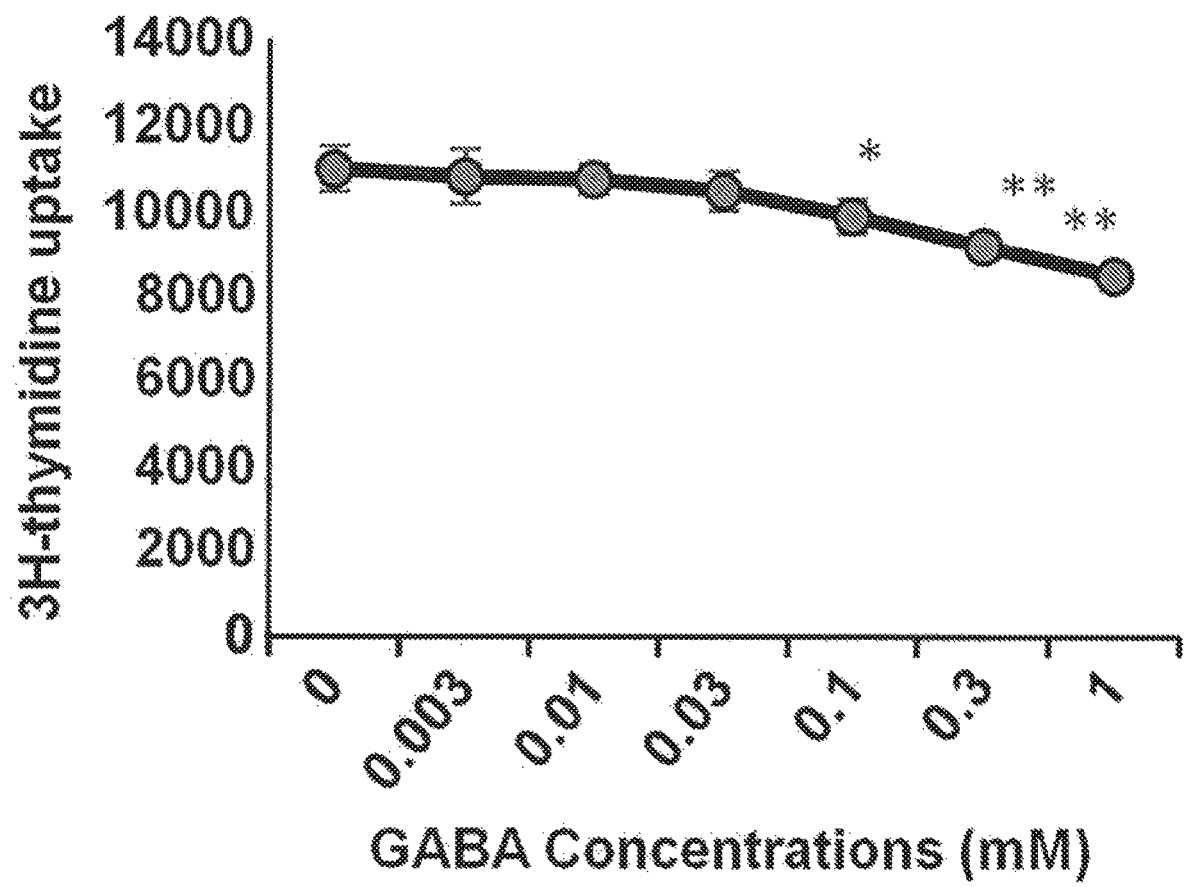
FIG. 1 shows the effect of GABA alone on the recall responses to HEL. A significant inhibitory effect on T cell proliferation was observed at GABA levels of 0.01-1 mM, consistent with our previous work. Ordinate 3H-thymidine uptake, as expressed in cpm (counts per minute). Abscissa: GABA concentrations as expressed in mM.
Figure 2:
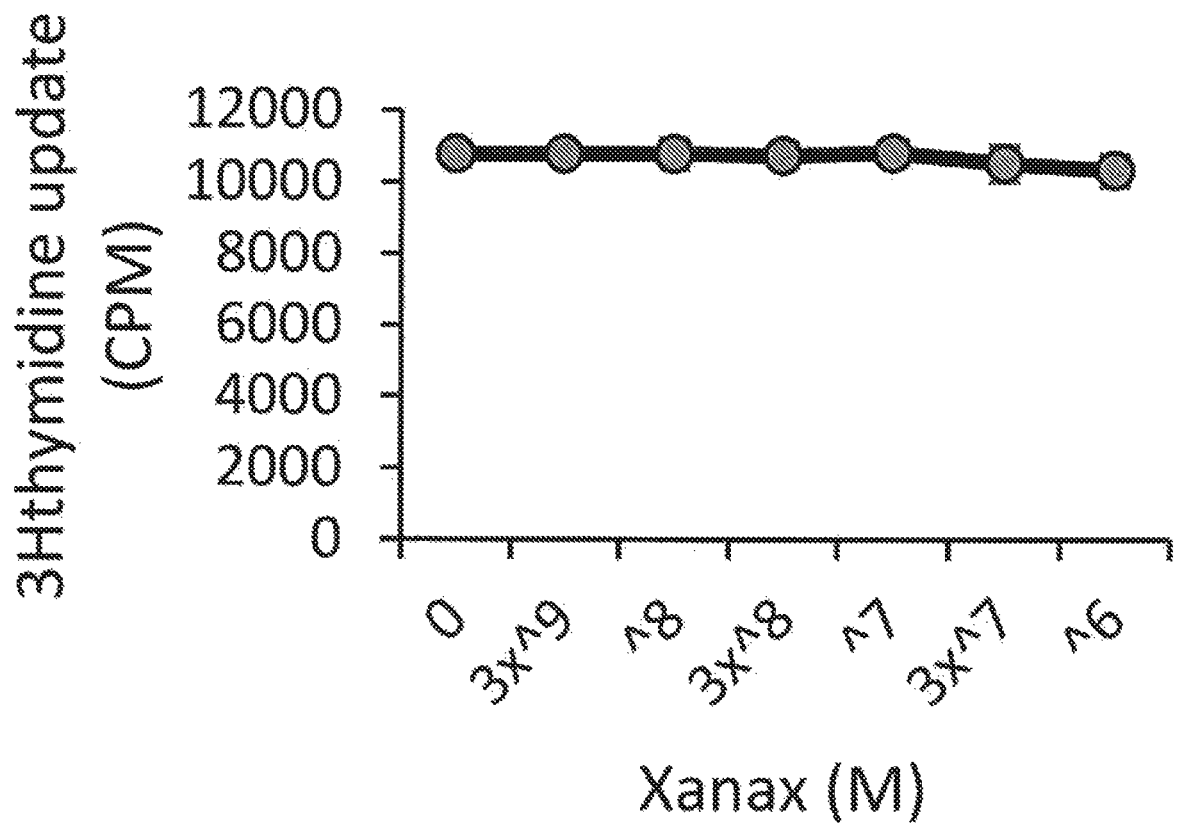
FIG. 2 shows that alprazolam (Xanax) alone did not have a significant effect on T cell proliferation at any of the dosages tested. This is consistent with the requirement for GABA to activate the GABA-Rs and that immune cells (unlike B-cells) make insufficient GABA to do so. Ordinate.

FIG. 1 shows the effect of GABA alone on the recall responses to HEL. A significant inhibitory effect on T cell proliferation was observed at GABA levels of 0.01-1 mM. FIG. 2 shows that alprazolam (Xanax) alone did not have a significant effect on T cell proliferation at any of the dosages tested. This is consistent with the requirement for GABA to activate the GABA-Rs and that immune cells (unlike B-cells) make insufficient GABA to do so.

We then tested GABA alone, and GABA at different concentrations in combination with Xanax at different combinations. FIG. 3 shows that the combination of GABA and Xanax more effectively inhibits immune cell proliferation (inflammatory response) in response to HEL. Note that GABA alone only had a significant inhibitory effect at 0.1-1.0 mM (light blue line). In contrast, when GABA was combined with Xanax at $1 \times 10^{-6}$ M (orange line), the combination was effective when GABA was present at just 0.01 mM, a ten-fold lower level than the lowest effective GABA (alone) dose. Also, note that, while GABA alone had a significant inhibitory effect at 0.1-1.0 mM, the inhibitory effect of GABA at 0.1-1 mM was significantly greater at each dose in the presence of Xanax at $1 \times 10^{-7}$ M, and an even greater when these dosages of GABA were combined with $3 \times 10^{-7}$ M Xanax. Thus, Xanax augmented the inhibitory effect of GABA on inflammatory immune responses, and their combination had greater inhibitory effect than either drug alone.

Without being bound to a particular theory it is believe these observations will extend to other GABA-R PAMs. Accordingly, in certain embodiments the of combined exogenous GABA or other GABA-R agonist together with a PAM is used to inhibit inflammatory responses. It is believed that this this combination will enable effective treatments with lower dosages of either, or both, drugs. Additionally, it is believed that this combination will more effectively promote regulatory responses.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of reducing an inflammatory immune response and/or promoting a regulatory immune response in a mammal, said method comprising administering to said mammal the $GABA_A$ receptor positive allosteric modulator (PAM) alprazolam and the GABA receptor activating ligand GABA, wherein the dose of GABA would be sufficient to achieve a reduction of an inflammatory immune response and/or promotion of a regulatory immune response when used alone, and the dose of alprazolam is sufficient to increase the reduction of an inflammatory immune response and/or promotion of a regulatory immune response, and wherein the combination of said alprazolam and GABA is more effective to reduce an inflammatory immune response and/or to promote a regulatory immune response in said mammal than when either agent is administered alone.

2. The method of claim 1, wherein said reduction in an inflammatory immune response or promotion of a regulatory immune response comprises a downregulation of one or more inflammatory cytokines or chemokines selected from the group consisting of IL-1, IL-12, IL-6, IL-17, tumor necrosis factor (TNF), interferon gamma (IFN-γ), granulocyte-macrophage colony stimulating factor (GMCSF), and IL-23.

3. The method according to claim 1, wherein said reduction in an inflammatory immune response or promotion of a regulatory immune response comprises a reduction of one or more inflammation-related T-cell types.

4. The method according to claim 1, wherein said mammal is a human.

5. The method of claim 4, wherein said mammal is a human diagnosed with type I diabetes.

6. The method of claim 4, wherein said mammal is diagnosed as pre-diabetic.

7. The method according to claim 1, wherein said mammal is a non-human mammal.

8. The method according to claim 1, wherein said GABA receptor activating ligand and said PAM act synergistically to reduce an inflammatory immune response and/or to promote a regulatory immune response.

9. The method of claim 1, wherein said alprazolam is administered at a dosage less than that used to treat used to treat an anxiety disorder, a panic disorder, and/or anxiety caused by depression.

10. The method of claim 1, wherein said alprazolam is administered as an immediate release tablet less than 1.5 mg orally per day or less than 1.0 mg orally per day, or less than 0.5 mg orally per day, or as an extended release tablet less than 0.5 mg orally per day, or less than about 0.4 mg orally per day or less than about 3 mg orally per day.

11. The method according to claim 1, wherein said method is used to treat an inflammatory disease.

12. The method of claim 11, wherein said method is used to treat a disease selected from the group consisting of type I diabetes (T1D), rheumatoid arthritis, systemic lupus erythematosus, myasthenia gravis, and multiple sclerosis.

13. The method according to claim 1, wherein said method is used to prevent or lessen graft rejection in a subject receiving a tissue graft.

14. The method according to claim 1 wherein said method is used to reduce an allergic response.

15. The method according to claim 1, wherein alprazolam is administered at a dose below that used for CNS indications.

* * * * *